United States Patent [19]

Miyoshi et al.

[11] Patent Number: 4,529,642

[45] Date of Patent: Jul. 16, 1985

[54] MOISTURE SENSITIVE RESISTIVE ELEMENT

[75] Inventors: Shuji Miyoshi, Osaka; Takashi Sugihara, Tenri; Masaya Hijikigawa, Yamatokoriyama, all of Japan

[73] Assignee: Sharp Kabushiki Kaisha, Osaka, Japan

[21] Appl. No.: 595,407

[22] Filed: Mar. 30, 1984

Related U.S. Application Data

[62] Division of Ser. No. 393,339, Jun. 29, 1982, abandoned.

[30] Foreign Application Priority Data

Jul. 8, 1981 [JP] Japan .................. 56-107292
Jul. 8, 1981 [JP] Japan .................. 56-107293

[51] Int. Cl.³ .................. H01L 7/00; B32B 15/08
[52] U.S. Cl. .................. 428/201; 428/913
[58] Field of Search .................. 428/913, 201, 210

[56] References Cited

U.S. PATENT DOCUMENTS

| | | | |
|---|---|---|---|
| 2,445,586 | 7/1948 | Simons | 428/913 X |
| 2,527,300 | 10/1950 | Dudley | 526/287 X |
| 2,908,595 | 10/1959 | Kohl | 428/913 X |
| 2,976,188 | 3/1961 | Kohl | 428/913 X |
| 3,265,536 | 8/1966 | Miller et al. | 525/57 X |
| 3,336,271 | 8/1967 | Durocher | 526/240 X |
| 3,453,143 | 7/1969 | Meixner et al. | 428/913 X |
| 3,559,456 | 2/1971 | Lomker et al. | 73/29 |
| 4,386,336 | 5/1983 | Kinomoto et al. | 428/913 X |

FOREIGN PATENT DOCUMENTS

| | | | |
|---|---|---|---|
| 810391 | 3/1959 | United Kingdom . | |
| 1188183 | 4/1970 | United Kingdom . | |
| 1231602 | 5/1971 | United Kingdom . | |
| 1388060 | 3/1975 | United Kingdom | 428/913 |
| 2048921 | 12/1980 | United Kingdom . | |

Primary Examiner—George F. Lesmes
Assistant Examiner—Nancy A. B. Swisher
Attorney, Agent, or Firm—Birch, Stewart, Kolasch & Birch

[57] ABSTRACT

A moisture sensitive resistive element includes a substrate made of an electrically non-conductive material, first and second electrodes deposited on the substrate in a spaced relation to each other, and a moisture sensitive film deposited on the substrate covering both the first and second electrodes. The moisture sensitive film is formed by a material given by a formula: $[-CH(C_6H_4SO_3X)-CH_2-]_n$ wherein X is any one of a hydrogen atom, metal atom, ammonium, urea, triethylenediamine, tetramethyleneguanidine and hexamethylenediamine, or formed by a mixture of the above material with a hydrophilic polymer which is any one selected from a group consisting of polyvinyl alcohol, methyl cellulose and polyamide resin.

1 Claim, 3 Drawing Figures

MOISTURE SENSITIVE RESISTIVE ELEMENT

This application is a divisional of copending application Ser. No. 393,339, filed on June 29, 1982, now abandoned.

BACKGROUND OF THE INVENTION

1. Field of the Invention

The present invention relates to a moisture sensitive resistive element and, more particularly, to an improved moisture sensitive resistive element of thin or thick film type which is sensitive to change of moisture content, or humidity, in the atmosphere in wide range covering 0% to 100% of relative humidity and has a quick response to such a humidity change to vary its internal ohmic resistance, a high reproducibility of moisture sensitive characteristic, and a high stability for a long period of time.

2. Description of the Prior Art

The moisture sensitive resistive element is an electric element which changes its internal ohmic resistance relative to the moisture content, or humidity, change in the atmosphere. According to the prior art, the moisture sensitive resistive element is formed by, for example: (1) a metallic oxide film or sintered metallic oxide material, such as iron oxide ($Fe_2O_3$ or $Fe_3O_4$) or tin dioxide ($SnO_2$); (2) a material containing electrolyte salt, such as lithium chloride (LiCl); (3) a moisture absorbent, or hygroscopic, resin or high polymer film in which fiber or fine particles of electric conductive material, such as carbon particles are dispersed; (4) a device utilizing a temperature sensitive element, such as thermistor; or (5) a hydrophilic polymer film.

In general, a moisture sensitive resistive element utilizing a metallic oxide has a high heat resistance and a high response to humidity change, but has such a disadvantage that, particularly in the case of sintered metallic oxide material, the moisture sensitive characteristic is highly dependent upon structural factors, such a surface area, the density of sintered material, and the size of a metallic oxide particle, and, therefore, the sintered metallic oxide material has a poor interchangeability and reproducibility of the moisture sensitive characteristic.

As to the moisture sensitive resistive element containing electrolyte salt, such as lithium chloride, a range of humidity which a single moisture sensitive resistive element can detect is narrow and, therefore, it is necessary to provide two or more elements sensitive to different humidity ranges to enable the moisture detection over an entire range covering from 0% to 100% of relative humidity. Furthermore, when the moisture sensitive resistive element of this type is disposed in a high humidity atmosphere, such as in an atmosphere having 90% to 95% of relative humidity, for a long period of time, there may occur an eluation or dilution of electrolyte salt and, as a result, the moisture sensitive characteristic becomes very poor and shortens the life of the element.

As to the moisture sensitive resistive element comprising electric conductive particles of fibers dispersed in a moisture absorbent resin, the degree of resistance change is very sharp under a high humid atmosphere, but it is very dull under a low humid atmosphere. Although this type of element is suitable for use in a dew detecting device, it is not suitable for detecting a moisture in a wide humidity range.

As to the moisture sensitive resistive element utilizing a temperature sensitive element, such as a thermistor, the moisture content in the atmosphere is detected indirectly by the temperature change of a self-heated thermistor, utilizing a fact that the heat conductivity of gas or air changes dependently on the amount of water vapor contained therein. This type of moisture sensitive resistive element may be used for detecting an absolute humidity but has such a disadvantage that the element is susceptible to surrounding temperature and wind.

As to the moisture sensitive resistive element using a hydrophilic polymer film, there are many advantages. For example: the humidity range which the element can detect is wide; the response to the humidity change is very fast; the structure of the element is rather simple; and the element can readily be manufactured at low cost. This type of element, however, has a poor resistance to moisture and water and, therefore, its life is very short.

SUMMARY OF THE INVENTION

The present invention has been developed with a view to substantially solving the above described disadvantages and has for its essential object to provide an improved moisture sensitive resistive element having an improved resistance to moisture and water with a high reliability to the moisture sensitive characteristic.

It is also an essential object of the present invention to provide an improved moisture sensitive resistive element of a thin or thick film type which has a high sensitivity over an entire range of relative humidity from 0% to 100%.

In accomplishing these and other objects, an improved moisture sensitive resistive element according to the present invention comprises a substrate made of electrically non-conductive material, a pair of electrodes deposited on the substrate in a spaced relation to each other, and a moisture sensitive film deposited on the substrate covering both the pair of electrodes.

According to one preferred embodiment of the present invention the moisture sensitive film is formed by a material given by a formula: $[-CH(C_6H_4SO_3X)-CH_2-]_n$ wherein X is any one of a hydrogen atom, metal atom, ammonium, urea, triethylenediamine, tetramethyleneguanidine and hexamethylenediamine.

According to another preferred embodiment, the moisture sensitive film is formed by a mixture of the above material with a hydrophilic polymer which is any one selected from a group consisting of polyvinyl alcohol, methyl cellulose and a polyamide resin.

BRIEF DESCRIPTION OF THE DRAWINGS

These and other objects and features of the present invention will become apparent from the following description taken in conjunction with preferred embodiments thereof with reference to the accompanying drawings in which.

DETAILED DESCRIPTION OF THE PREFERRED EMBODIMENTS

Figure 1:
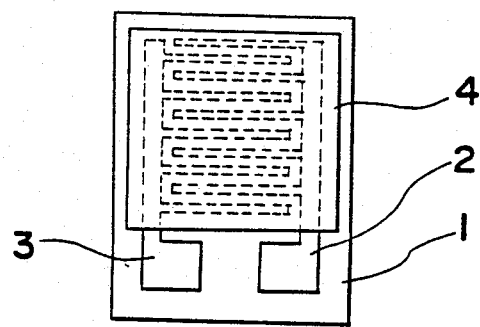
FIG. 1 is a top plan view diagrammatically showing a fundamental structure of a moisture sensitive resistive element according to the present invention.

Referring to FIG. 1, there is shown diagrammatically a fundamental structure of a moisture sensitive resistive element of the present invention. The moisture sensitive resistive element comprises a substrate 1 made of a high electric insulation material, such as alumina or glass, and a pair of comb-shaped electrodes 2 and 3 interlaced with each other. The electrodes 2 and 3 are deposited on the substrate 1 by any known method, such as vapor deposition or sputtering.

According to the first embodiment, the moisture sensitive resistive element further comprises a moisture sensitive film 4 comprising a polyelectrolyte deposited on the electrodes 2 and 3 by a method of coating. Here, the polyelectrolyte material is either a polystyrenesulfonic acid or a polystyrenesulfonate.

One example of the moisture sensitive film 4 of the first embodiment has a thickness of about 1 micrometer, and is formed by the steps of coating an aqueous solution containing 30% of ammonium polystyrenesulfonate of a molecular weight of more than about 100,000 over the substrate 1 using a spinner and, thereafter, the coated film is sintered under a temperature of about 100° C. According to a preferred embodiment, a protection layer made of a polymer and having a high moisture permeability is coated on the moisture sensitive film 4. However, the moisture sensitive film 4 will function without such a protection layer, with no problem.

Figure 2:
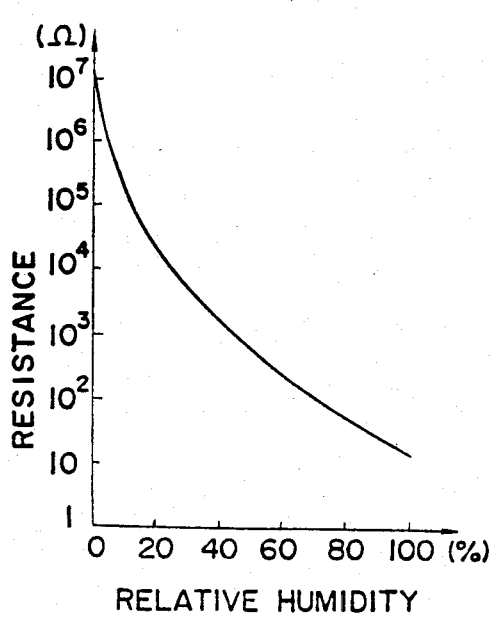
FIG. 2 is a graph showing the relation between relative humidity and resistance (moisture sensitive characteristic) of a moisture sensitive resistive element according to one embodiment of the present invention.

Referring to FIG. 2, there is shown a graph of the moisture sensitive characteristic of the moisture sensitive resistive element described above under atmosphere temperature 30° C., in which the abscissa and ordinate represent relative humidity in percent and ohmic resistance of the moisture sensitive resistive element, respectively. As is apparent from the graph, the moisture sensitive resistive element according to the first embodiment shows an ohmic resistance change over an entire range of relative humidity from 0% to 100%. And particularly in a range above 20% to 30% of the relative humidity, the resistance of the element is below 10K ohms. This figure is very pleasing from a practical view point.

Furthermore, the moisture sensitive resistive element described above showed an excellent response with respect to moisture change. For example, under the atmosphere of a relative humidity 40% to 80%, both absorption and desorption of the moisture with respect to the humidity change were carried out within a few seconds. Even if there is a protection layer over the moisture sensitive film, the response is delayed only a very little.

In addition, the moisture sensitive resistive element described above has a stable moisture sensitive characteristic. In the tests, the moisture sensitive resistive element of the invention was disposed under a atmosphere temperature of 30° C. and relative humidity of 80% for a long period of time. After this period, the moisture sensitive film 4 showed no change in its structure.

As stated above, the moisture sensitive film 4 according to the first embodiment is formed by a polyelectrolyte which is either a polystyrenesulfonic acid or a polystyrenesulfonate. In the above example, an ammonium polystyrenesulfonate is employed as the polyelectrolyte. It is to be noted that in place of the polyelectrolyte, a salt other than ammonium polystyrenesulfonate can be employed. For example, it is possible to employ a polymeric film of a formula $[-CH(C_6H_4SO_3X)-CH_2-]_n$ wherein X represents a metal atom, urea, triethylenediamine, tetramethyleneguanidine or hexamethylenediamine, and n is a polymerization degree which can be any number greater than 50. It has been found that the moisture sensitive film 4 formed of any one of the above described polymeric films showed the same moisture sensitive characteristic as that described above in connection with FIG. 2.

Next, a moisture sensitive resistive element according to a second embodiment is described. The moisture sensitive resistive element of the second embodiment superficially has the same structure as that shown in FIG. 1, but when compared with the first embodiment, the chemical structure of the moisture sensitive film 4 is different. The moisture sensitive film 4 of the second embodiment comprises a mixture of a polyelectrolyte and a hydrophilic polymer. For the polyelectrolyte, a polystyrenesulfonic acid or a polystyrenesulfonate is employed, and for the hydrophilic polymer, a polyvinyl alcohol, a methyl cellulose, a polyamide resin or the like is employed.

One example of the moisture sensitive film 4 of the second embodiment has a thickness of about 1 micrometer, and is formed by the steps of mixing an aqueous solution containing 30% of ammonium polystyrenesulfonate having a molecular weight of more than about 100,000 and an aqueous solution containing polyvinyl alcohol, coating the mixture over the substrate 1 using a spinner and, thereafter, the coated film is sintered under a temperature about 100° C. As in the first embodiment, a protection layer made of a polymer and having a high moisture permeability is coated on the moisture sensitive film 4. However, the moisture sensitive film 4 functions without such a protection layer with no problem.

Figure 3:
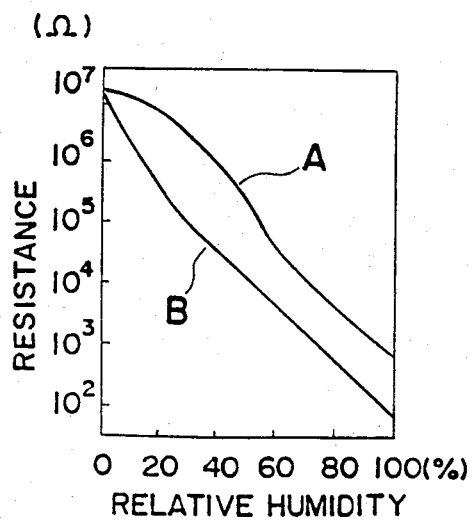
FIG. 3 is a graph showing the moisture sensitive characteristic of a moisture sensitive resistive element according to another embodiment of the present invention.

Referring to FIG. 3, there is shown a graph of moisture sensitive characteristic of the moisture sensitive resistive element of the second embodiment under atmosphere temperature 30° C., in which the abscissa and the ordinate represent relative humidity in percent and ohmic resistance of the moisture sensitive resistive element, respectively. In the graph, curves A and B are obtained when the moisture sensitive film 4 is formed by a mixture of ammonium polystyrenesulfonate and polyvinyl alcohol at a ratio of 2:1, and by the same mixture but at a ratio of 4:1, respectively. As apparent from the graph, the moisture sensitive characteristic of the element according to the second embodiment can be changed to present a desired curve by the change of mixture ratio of ammonium polystyrenesulfonate and polyvinyl alcohol.

Furthermore, by the use of the mixture of ammonium polystyrenesulfonate and polyvinyl alcohol, the water resistance of the moisture sensitive resistive element according to the second embodiment is improved.

As stated above, the moisture sensitive film 4 according to the second embodiment is formed by a mixture of a polyelectrolyte, which is either one of a polystyrenesulfonic acid or a polystyrenesulfonate, and a hydrophilic polymer, which is either one of a polyvinyl alcohol, a methyl cellulose, a polyamide resin or the like. In the above example, an ammonium polystyrenesulfonate is employed as the polyelectrolyte. It is to be noted that a suitable salt other than ammonium polystyrenesulfonate can be employed. For example, it is possible to employ a polymeric film of a formula $[-CH(C_6H_4SO_3X)-CH_2-]_n$ wherein X represents metal atom, urea, triethylenediamine, tetramethyleneguanidine or hexamethylenediamine. It is to be noted that the polymerization degree n can be any number greater than 50. It has been found that the moisture sensitive film 4 formed by any combination of the above described polyelectrolyte and hydrophilic polymer showed the same moisture sensitive characteristic as that described above in connection with FIG. 3.

It is to be noted that the thickness of the moisture sensitive film 4, which has been described as 1 micrometer, can be greater than or less than 1 micrometer, and preferably not greater than 10 micrometers.

It is also to be noted that the moisture sensitive resistive element according to the second embodiment has the same advantages as those of the first embodiment. More particularly, the moisture sensitive resistive element of the second embodiment responds to the entire range of relative humidity from 0% to 100% in a very short time and, at the same time, its moisture sensitive characteristic is very stable with respect to the environmental change. In addition, the element according to the second embodiment has such an advantage that the moisture sensitive characteristic can be changed to present a desired curve by the change of mixture ratio of polyelectrolyte and hydrophilic polymer.

Although the present invention has been fully described with reference to several preferred embodiments, many modifications and variations thereof will now be apparent to those skilled in the art, and the scope of the present invention is therefore to be limited not by the details of the preferred embodiments described above, but only by the terms of the following claims.

What is claimed is:

1. A highly stable moisture sensitive electrically resistive element capable of detecting and measuring moisture variation and contact under ambient conditions ranging from 0 to 100% relative humidity comprising:
   a substrate made of a electrically non-conductive material;
   first and second electrodes superimposed on said substrate in a spaced relationship to each other; and
   a moisture sensitive film deposited on the substrate covering both the pair of electrodes of polystyrenesulfonic acid comprising a polymeric material having a formula:

$$[-CH(C_6H_4SO_3X)-CH_2-]_n$$

wherein X is any one of a hydrogen atom, metal atom, ammonium, urea, triethylenediamine, tetramethyleneguanidine and hexamethylenediamine wherein n is greater than 50;
   said electrically resistive element being capable of responding quickly to said broad humidity range to vary its internal ohmic resistance.
   * * * * *